United States Patent [19]

Husslein et al.

[11] Patent Number: 4,789,747
[45] Date of Patent: Dec. 6, 1988

[54] CONTROL OF UNWANTED PLANT GROWTH WITH 2-ARYLOXY-2-AZOLYLALKANECARBOXAMIDES, HERBICIDES CONTAINING THEM, AND THE MANUFACTURE THEREOF

[75] Inventors: Gerd Husslein, Bad Durkheim; Eberhard Ammermann, Ludwigshafen; Gerhard Hamprecht, Weinheim; Bruno Wuerzer, Otterstadt, all, Fed. Rep. of Germany

[73] Assignee: BASF Aktiengesellschaft, Ludwigshafen, Fed. Rep. of Germany

[21] Appl. No.: 940,222

[22] Filed: Dec. 8, 1986

Related U.S. Application Data

[63] Continuation of Ser. No. 321,640, Nov. 16, 1981, abandoned, and a continuation-in-part of Ser. No. 310,402, Oct. 9, 1981, Pat. No. 4,515,623.

[30] Foreign Application Priority Data

Nov. 5, 1980 [DE] Fed. Rep. of Germany ....... 3041702

[51] Int. Cl.$^4$ .......................................... C07D 249/04
[52] U.S. Cl. ................................................... 548/262
[58] Field of Search ................... 54/8, 262, 269, 341, 54/375

[56] References Cited

FOREIGN PATENT DOCUMENTS

0010298 4/1980 European Pat. Off. .
0010270 4/1980 European Pat. Off. .
2550566 5/1976 Fed. Rep. of Germany .
2720654 11/1978 Fed. Rep. of Germany .

OTHER PUBLICATIONS

R. Wegler, Chemie der Pflanzenschutz- und. Schädlingsbekämpfungsmittel, vol. 5, (1977), p. 180.

*Primary Examiner*—Catherine L. Mills
*Attorney, Agent, or Firm*—Keil & Weinkauf

[57] ABSTRACT

A process for combating the growth of unwanted plants, wherein the soil or the plants are treated with a compound of the formula

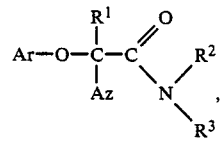

where Ar denotes substituted or unsubstituted phenyl or naphthyl, $R^1$ denotes hydrogen or methyl, $R^2$ denotes hydrogen or alkyl, $R^3$ denotes alkyl, cycloalkyl, alkenyl, alkynyl, or substituted aralkyl, and Az denotes substituted or unsubstituted pyrazole, imidazole or triazole, or a metal complex thereof, and herbicides for carrying out the process.

2 Claims, No Drawings

CONTROL OF UNWANTED PLANT GROWTH WITH 2-ARYLOXY-2-AZOLYLALKANECARBOXA-MIDES, HERBICIDES CONTAINING THEM, AND THE MANUFACTURE THEREOF

This application is a continuation of application Ser. No. 321,640 filed on Nov. 16, 1981 and a continuation-in-part of application Ser. No. 310,402, filed Oct. 9, 1981 now U.S. Pat. No. 4,515,623.

The present invention relates to processes for combating the growth of unwanted plants with 2-aryloxy-2-azolylalkanecarboxamides, herbicides containing them, and processes for the manufacture thereof.

The use of phenoxyalkanecarboxylic acid derivatives, e.g., the diemthylamine salt of 2,4-dichlorophenoxyacetic acid, as herbicides has been disclosed (R. Wegler, Chemie der Pflanzenschutz- and Schädlingsbekämpfungsmittel ("Chemistry of crop protection agents and pesticides"), Vol. 5, Herbizide ("Herbicides"), 1977, p. 180). Their particular advantage is that they combat broadleaved plant species while leaving grasses and grassy crop plants substantially unaffected.

It has also been disclosed that 2-aryloxy-2-azolylalkanecarboxamides have a fungicidal action (German laid-open application DE-OS No. 27 20 654). However, a herbicidal action of the compounds is not known.

We have now found that compounds of the formula

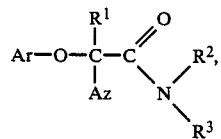

where Ar denotes substituted or unsubstituted phenyl or naphthyl, $R^1$ denotes hydrogen or methyl, $R^2$ denotes hydrogen or $C_1$–$C_{10}$-alkyl, $R^3$ denotes $C_1$–$C_{10}$-alkyl, cycloalkyl, cyclopropylmethyl, alkenyl, alkynyl, or unsubstituted or halogen-substituted aralkyl, and Az denotes unsubstituted or halogen- or methyl-substituted pyrazole, imidazole or triazole, and the metal complexes thereof, exhibit herbicidal and growth-regulating properties.

The compounds are effective both on broadleaved and grassy plants.

The manufacture of the compounds of the formula I is known: either appropriate 2-aryloxy-2-haloalkanecarboxamides are reacted with azoles; 2-aryloxy-2-azolylalkanecarboxylic acid esters are amidated (German laid-open application DE-OS No. 27 20 654); or 2-aryloxy-2-azolylalkanecarboxylic acids—if desired after having been activated with, for example, thionyl chloride or thionyl diazoles—are reacted with amides (German laid-open application DE-OS No. 28 46 038).

In formula I, Ar preferably denotes phenyl mono- or polysubstituted by halogen, $C_1$–$C_4$-alkyl, nitro, cyano, trifluoromethyl, chlorodifluoromethyl, trifluoromethylsulfonyl, benzyl or phenyl, e.g., 2-methyl-4-chlorophenyl, 2,4-dichlorophenyl, 3,5-dichlorophenyl, 2-bromo-4-chlorophenyl, 3,4-dichlorophenyl, 2,4,5-trichlorophenyl, 2,4-dinitrophenyl, 2-chloro-4-cyanophenyl, 4-fluorophenyl, 3-trifluoromethylphenyl, 3,5-dimethylphenyl, 4-benzylphenyl, o-diphenyl, p-diphenyl, 3-tert-butylphenyl and 4-tertbutylphenyl; or unsubstituted or halogen-substituted naphthyl, e.g., α-naphthyl, β-naphthyl; $R^1$ denotes hydrogen or methyl; $R^2$ preferably denotes hydrogen, methyl or ethyl; $R^3$ preferably denotes $C_1$–$C_{10}$-alkyl or $C_3$–$C_8$-cycloalkyl, e.g., methyl, ethyl, n-propyl, iospropyl, cyclopropyl, n-butyl, isobutyl, tert-butyl, cyclobutyl, n-pentyl, 2-pentyl, 3-pentyl, tert-amyl, neopentyl, 2-methylbutyl, 3-methylbutyl, 3-methyl-2-butyl, cyclopentyl, n-hexyl, 4-methyl-2-pentyl, 2,3-dimethylbutyl, 2-methyl-1-pentyl, 2-hexyl, 3-hexyl, 3-methyl-2-pentyl, 3-methylpentyl, 4-methylpentyl, 3-methyl-3-pentyl, 4,4-dimethylbutyl, cyclohexyl, heptyl, 2-heptyl, 3-heptyl, 4-heptyl, cycloheptyl, 1-octyl, 3-octyl, 4-octyl, 5-octyl, 5-ethyl-2-heptyl, 2,6-dimethyl-4-heptyl, 2,4-dimethyl-3-pentyl, 3-methyl-2-heptyl, nonyl, 6-ethyl-3-octyl, 2-methyl-2-pentyl, 2,3-dimethyl-2-butyl, 2-methyl-2hexyl, 3-ethyl-3-pentyl, 3-methyl-3-hexyl, 2,3-dimethyl-2-butyl, 2,4-dimethyl-2-pentyl, 2,2,3-trimethyl-3-butyl, 2-methyl-2-heptyl, 4-methyl-4-heptyl, 2,4-dimethyl-2-hexyl, 2-methyl-2-octyl, 1-methyl-1-cyclopentyl, 1-methyl-1-cyclohexyl, 1-ethyl-1-cyclohexyl, and 2-methylnorborn-2-yl; $C_3$–$C_6$-alkenyl, e.g., allyl, methallyl, crotyl, 2-methylbut-2-en-1-yl, 2-methylbut-1-en-3-yl, hex-5-en-1-yl, and 2-methylbut-1-en-4-yl; $C_3$–$C_6$-alkynyl, e.g., propargyl, but-1-yn-3-yl, but-2-yn-1-yl, and 3-methylbut-1-yn-3-yl; and unsubstituted or halogen-substituted benzyl having 1 to 2 carbon atoms in the alkyl moiety and 6 to 10 carbon atoms in the aryl moiety, e.g., benzyl, p-chlorobenzyl, and α-phenylethyl; and Az preferably denotes unsubstituted or halogen- or methyl-substituted triazole.

In a particularly preferred class of compounds of the formula I, Ar denotes phenyl mono- or polysubstituted by halogen and/or methyl, $R^1$ denotes hydrogen, $R^2$ denotes hydrogen, and $R^3$ denotes branched $C_3$–$C_7$-alkyl, e.g., isopropyl, isobutyl, tert-butyl, tert-amyl and 2,4-dimethylpent-3-yl.

Metal complexes are the complexes with salts of metals, e.g., copper, cobalt and chromium. The metal complexes are prepared by reaction of metal-free compounds with metal salts, e.g., in an organic solvent for the compound.

The active ingredients contain an asymmetrical carbon atom, and therefore form optically active isomers which may be prepared in conventional manner from the racemates formed during manufacture. The present invention relates not only to the racemates, but also to the individual optically active isomers.

Examples of the active ingredients are given in the following table.

| No. | Ar | Az | $R^1$ | $R^2$ | $R^3$ | M.p. [°C.] |
|---|---|---|---|---|---|---|
| 1 | 2,4-Dichlorophenyl | triazolyl | H | H | i-$C_3H_7$ | 50–53 |
| 2 | " | " | $CH_3$ | " | " | |
| 3 | " | " | H | " | tert. $C_4H_9$ | 107–108 |

| No. | Ar | Az | $R^1$ | $R^2$ | $R^3$ | M.p. [°C.] |
|---|---|---|---|---|---|---|
| 4 | " | " | " | " | 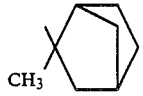 | 103–106 |
| 5 | " | " | " | " | —CH(i-$C_3H_7$)$_2$ | 117–120 |
| 6 | " | " | " | " |  | 92–6 |
| 7 | " |  | " | " | tert. $C_4H_9$ | oil |
| 8 | " | 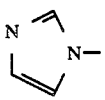 | " | " | " | oil |
| 9 | " |  | " | " | —C($CH_3$)$_2$C≡CH | 112–115 |
| 10 | " | " | " | $CH_3$ | $CH_3$ | 148–150 |
| 11 | " | " | " | " | $CH_2CH(CH_3)_2$ | 106–108 |
| 12 | " | " | " | H | 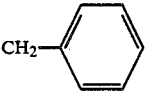 | 71–75 |
| 13 | 4-Chlorophenyl | " | " | " | tert. $C_4H_9$ | 176–180 |
| 14 | 2,4,5-Trichlorophenyl | " | " | " | " | 128–131 |
| 15 | 4-Fluorophenyl | " | " | " | " | 90–94 |
| 16 | 4-Diphenyl | " | " | " | " | 114–118 |
| 17 | 2-Diphenyl | " | " | " | " | 142–146 |
| 18 | 4-Chlorophenyl | " | " | " | C($CH_3$)$_2$C≡CH | 74–78 |
| 19 | 3,5-Dimethylphenyl | " | " | " | tert. $C_4H_9$ | 131–133 |
| 20 | Phenyl | 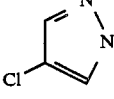 | " | " | " | 142–144 |
| 21 | " |  | " | " | " | 105–106 |
| 22 | " |  | " | " | " | oil |
| 23 | " |  | " | " | " | 101–103 |
| 24 | 2-Methyl-4-chlorophenyl | " | " | " | " | 119–122 |
| 25 | 4-tert.-butylphenyl | " | " | " | " | 126–129 |
| 26 | 4-Benzylphenyl | " | " | " | " | 102–105 |
| 27 | α-Naphthyl | " | " | $CH_3$ | $CH_3$ | 90–92 |
| 28 | " | " | " | $C_2H_5$ | $C_2H_5$ | 82–83 |
| 29 | " | " | " | H | tert. $C_4H_9$ | 110–114 |
| 30 | 3-Trifluoromethylphenyl | " | " | " | " | 129–132 |

-continued

| No. | Ar | Az | R¹ | R² | R³ | M.p. [°C.] |
|---|---|---|---|---|---|---|
| 31 | 2,4-Dichlorophenyl | " | " | " | CH₂—CH(CH₃)₂ | 74–76 |
| 32 | " | " | " | " | tert. C₄H₉ CuCl₂ complex | 172–176 |
| 33 | 3-tert.-butylphenyl | " | " | " | tert.C₄H₉ | 97–99 |
| 34 | 3,5-Dimethylphenyl | " | " | " | —C(CH₃)₂—C≡CH | 96–98 |
| 35 | " | " | " | " | Benzyl | 97–98 |
| 36 | 3,5-Dichlorophenyl | " | " | " | tert. C₄H₉ | 104–106 |
| 37 | " | " | " | " | Benzyl | 106–108 |
| 38 | " | " | " | " | —C(CH₃)—C≡CH | |
| 39 | 2-Cl-3,5-dimethylphenyl (H₃C, Cl, H₃C substituted) | " | " | " | tert. C₄H₉ | 129–131 |
| 40 | " | " | " | " | —CH₂—C₆H₅ | 111–114 |
| 41 | 2,6-dimethylphenyl (H₃C, H₃C) | " | " | " | —CH(CH₃)—C₆H₅ | 118 |
| 42 | " | " | " | " | —CH(CH₃)—C₆H₅ (optically active isomer) | 105 |
| 43 | 2,4-Dichlorophenyl | " | " | " | —CH(CH₃)—C₆H₅ | 102–103 |
| 44 | " | " | " | " | —CH₂—(2-Cl-C₆H₄) | 102–105 |
| 45 | 2,5-diethylphenyl (H₅C₂, H₅C₂) | 1,2,4-triazolyl (N-N=N) | " | " | tert. C₄H₉ | 106–108 |
| 46 | 2,4-dimethoxyphenyl (CH₃O, CH₃O) | " | " | " | " | 140–144 |

-continued

| No. | Ar | Az | R¹ | R² | R³ | M.p. [°C.] |
|---|---|---|---|---|---|---|
| 47 | 3-ethyl-4-methylphenyl (H₅C₂, H₃C substituted benzene) | " | " | " | " | 85–89 |
| 48 | 2-bromo-1,3-dimethylphenyl (Br, H₃C, H₃C substituted benzene) | " | " | " | " | 107–112 |
| 49 | 2,3,5-trimethylphenyl (H₃C, CH₃, H₃C substituted benzene) | " | " | " | " | 103–107 |
| 50 | naphthyl | " | " | " | —CH₂—CH(CH₃)₂ | 105–107 |
| 51 | " | " | " | " | sec.-C₄H₉ | 128–130 |
| 52 | " | " | " | " | —CH(CH₃)₂ | 128–130 |
| 53 | " | " | " | " | cyclohexyl | 180–182 |
| 54 | 2,4,5-trichlorophenyl | " | " | " | —CH₂—cyclopropyl | 128–130 |
| 55 | " | " | " | " | sec.-C₄H₉ | 119–120 |
| 56 | " | " | " | " | —CH(CH₃)₂ | 118–119 |
| 57 | " | " | " | " | cyclohexyl | 105–108 |
| 58 | 2,3-dimethylphenyl | " | " | " | tert.-C₄H₉ | 79–80 |
| 59 | " | " | " | " | —CH(CH₃)₂ | 110–111 |
| 60 | " | " | " | " | cyclohexyl | 117–118 |

-continued
| No. | Ar | Az | R¹ | R² | R³ | M.p. [°C.] |
|---|---|---|---|---|---|---|
| 61 | " | " | " | " | 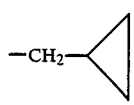 —CH₂— (cyclopropyl) | 167–168 |
| 62 | " | " | " | " | sec.-C₄H₉ | 100–102 |
| 63 | 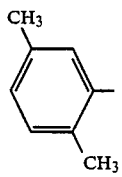 2,4-(CH₃)₂-C₆H₃ | 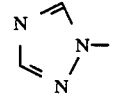 1,2,4-triazol-1-yl | " | " | i-C₃H₇ | 107–108 |
| 64 | " | " | " | " | sec.-C₄H₉ | 101–102 |
| 65 | " | " | " | " | 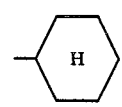 cyclohexyl | 89–90 |
| 66 | " | " | " | " | —CH₂— (cyclopropyl) | 143–145 |
| 67 | " | " | " | " | tert.-C₄H₉ | 76–77 |
| 68 | 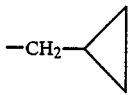 2,6-(CH₃)₂-C₆H₃ | " | " | " | i-C₃H₇ | 136 |
| 69 | " | " | " | " | sec.-C₄H₉ | 134 |
| 70 | " | " | " | " | 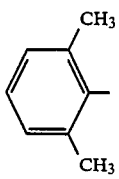 cyclohexyl | 146–148 |
| 71 | " | " | " | " | tert.-C₄H₉ | 94 |
| 72 | 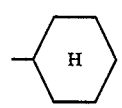 4-Cl-3-CH₃-C₆H₃ | " | " | " | i-C₃H₇ | 94–95 |
| 73 | " | " | " | " | sec.-C₄H₉ | 83 |
| 74 | " | " | " | " | 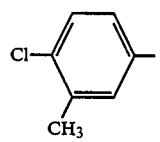 cyclohexyl | 110–112 |
| 75 | " | " | " | " | tert.-C₄H₉ | 99–100 |
| 76 | 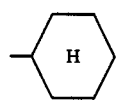 3,5-Br₂-C₆H₃ | " | " | " | " | 127–128 |
| 77 | " | " | " | " | i-C₃H₇ | 79–80 |
| 78 | " | " | " | " | sec.-C₄H₉ | 122–123 |

-continued

| No. | Ar | Az | R¹ | R² | R³ | M.p. [°C.] |
|---|---|---|---|---|---|---|
| 79 | 2,4-Cl, 3,5-(CH₃)₂-phenyl | " | " | " | cyclohexyl | 146–149 |
| 80 | " | " | " | " | i-C₃H₇ | 119–120 |
| 81 | 2,4,6-trichlorophenyl | " | " | " | tert.-C₄H₉ | 154 |
| 82 | " | " | " | " | i-C₃H₇ | 120 |
| 83 | " | " | " | " | sec.-C₄H₉ | 102–106 |
| 84 | " | " | " | " | cyclohexyl | 133 |
| 85 | " | " | " | " | —CH₂-cyclopropyl | 103 |
| 86 | 4-(tert.-butyl-O)-phenyl | " | " | " | tert.-C₄H₉ | 113 |
| 87 | 2,3-dichlorophenyl | " | " | " | " | |
| 88 | " | " | " | " | i-C₃H₇ | |
| 89 | " | " | " | " | sec.-C₄H₉ | |
| 90 | 2,5-dichlorophenyl | " | " | " | tert.-C₄H₉ | |
| 91 | " | " | " | " | i-C₃H₇ | |
| 92 | " | " | " | " | sec.-C₄H₉ | |
| 93 | 2,6-dichlorophenyl | " | " | " | tert.-C₄H₉ | |
| 94 | " | " | " | " | sec.-C₄H₉ | |
| 95 | " | " | " | " | i-C₃H₇ | |

| No. | Ar | Az | R¹ | R² | R³ | M.p. [°C.] |
|---|---|---|---|---|---|---|
| 96 | MeO-, MeO-, MeO- trisubstituted phenyl | " | " | " | " | |
| 97 | " | " | " | " | sec.-C₄H₉ | |
| 98 | " | " | " | " | tert.-C₄H₉ | |
| 99 | Cl, Cl, Cl trisubstituted phenyl | " | " | " | " | |
| 100 | " | " | " | " | i-C₃H₇ | |
| 101 | " | " | " | " | sec.-C₄H₉ | |
| 102 | naphthyl | " | " | " | tert.-C₄H₉ | |
| 103 | " | " | " | " | sec.-C₄H₉ | |
| 104 | " | " | " | " | i-C₃H₇ | |
| 105 | CH₃, CH₃, CH₃ trisubstituted phenyl | " | " | " | " | |
| 106 | " | " | " | " | sec.-C₄H₉ | |
| 107 | " | " | " | " | tert.-C₄H₉ | |
| 108 | Cl, CH₃, CH₃ trisubstituted phenyl | " | " | " | " | |
| 109 | " | " | " | " | i-C₃H₇ | |
| 110 | " | " | " | " | sec.-C₄H₉ | |
| 111 | CH₃, CH₃, CH₃ trisubstituted phenyl | " | " | " | " | |
| 112 | " | " | " | " | tert.-C₄H₉ | |
| 113 | " | " | " | " | i-C₃H₇ | |
| 114 | 2,4-dichlorophenoxyphenyl | " | " | " | tert.-C₄H₉ | |

The active ingredients can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines e.g., ethanolamine, dimethylformamide, and water; solid carriers, for example natural rock powders, e.g., kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

To initiate the herbicidal action, wetting agents, spreader-stickers and non-phytotoxic oils and oil concentrates may be added.

The herbicidal agents in general contain from 0.1 to 95% by weight of active ingredient, preferably from 5 to 90%.

Depending on the plants making up the weed flora, and their growth stages, application rates vary from 0.1 to 15, and preferably from 0.2 to 5, kg of active ingredient per hectare. The higher rates are to be used for total elimination of vegetation.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting, treating seed or watering.

Examples of such formulations are given below,

I. 90 parts by weight of compound 1 is mixed with 10 parts by weight of N-methyl-α-pyrrolidone. A mixture is obtained which is suitable for application in the form of very fine drops.

II. 80 parts by weight of compound 2 is mixed with 20 parts by weight of cyclohexanone. The mixture may be sprayed in the form of droplets.

III. 10 parts by weight of compound 3 is dissolved in a mixture consisting of 60 parts by weight of cyclohexanone, 20 parts by weight of isobutanol, and 10 parts by weight of the adduct of 40 moles of ethylene oxide to 1 mole of castor oil.

IV. 3 parts by weight of the compound of Example 2 is intimately mixed with 97 parts by weight of particulate kaolin. A dust is obtained containing 3% by weight of the active ingredient.

V. 30 parts by weight of the compound of Example 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VI. 20 parts of compound 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied alone or in the admixture among themselves or with other herbicides or other crop protection agents, e.g., agents for combating pests or phytopathogenic fungi or baceteria. The compounds may also be mixed with mineral salt solutions used to remedy nutritional or trace element deficiencies.

The action of the active ingredients on the growth of plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species.

In the preemergence treatment, the active ingredients were immediately applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which had been sown directly in the pots and had grown there were selected, or plants which had been grown separately as seedlings and transplanted to the experiment vessels a few days before treatment. The amounts of active ingredient applied in this treatment were 0.5 and 1.0 kg/ha, and in somne cases 3.0 kg/ha.

The agents used for comparison purposes were the dimethylamine salt of 2,4-dichlorophenoxyacetic acid (A), at the same rates (based on acid), and (2,4-dichlorophenoxy)-(1,2,4-triazol-1-yl)-acetic acid amide (B) (German laid-open application DE-OS No. 27 20 654), at the same rates.

No cover was placed on the vessels. The pots were set up in the greenhouse—species from warmer areas at from 20° to 30° C., and species from moderate climates at 15° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The results reveal, on postemergence application in the greenhouse, the expected herbicidal action of comparative agent A on broadleaved unwanted plants, combined with slight damage to grasses and the grassy crop plant barley. When applied in the same manner, comparative agent B had no action at all on most of the test plants, and only a slight action here and there. By contrast, active ingredient No. 19 had, no postemergence application in the greenhouse, an extremely widespread action on broadleaved and grassy plants. This action encompassed not only herbicidal (i.e., killing) effects, but also—in the case of grass species—predominantly a restriction in growth (i.e., reduced growth height).

In these experiments, compound No. 31 also exhibited, on postemergence application in the greenhouse, a much better herbicidal action than comparative agent B.

On pre- and postemergence application in the greenhouse, active ingredients Nos. 23, 3, 6, 30 and 1 exhibited a good herbicidal action.

In further greenhouse experiments, compounds Nos. 41, 39 and 36, applied postemergence at a rate of 0.5 kg/ha, had an action at first strongly inhibiting and then increasingly herbicidal, on both broadleaved and grassy plants.

The growth- and bioregulating properties of the active ingredients may be illustrated in a further greenhouse experiment with cotton. In this perennial crop, it is a disadvantage for vegetative and generative growth not to be complete at the end of the first season (i.e., within 1 year). It is also a drawback if defoliated cotton plants ready for harvesting start to sprout and turn green again. In a model experiment with budding and boll-forming cotton plants, compounds Nos. 19, 41 and 36, applied to the foliage at rates of 1.0 and 4.0 kg/ha, were able to prevent, or strongly inhibit, this undesirable further growth.

The active ingredients, or agents containing them, may be used pre- or postemergence, but are preferably applied to the foliage.

If the crop plants do not tolerate the active ingredients application techniques may be used in which the herbicidal or growth-regulating agents are sprayed from suitable equipment in such a manner that the sensitive parts of the crop plants are not touched, and the agents reach the soil or the unwanted plants growing beneath the crop plants (post-directed, lay-by treatment).

The amount of active ingredient or active acid applied depends on the season and the growth stage of the target plants, and varies from 0.1 to 15 kg/ha and more, the higher rates being particularly suitable for total elimination of vegetation.

To increase the spectrum of action and to achieve synergistic effects, the α-azolylalkanecarboxamides may be mixed and applied together with numerous representatives of other herbicidal or growth-regulating active ingredient groups. Examples of suitable mixture components are diazines, benzothiadiazinones, 2,6-dinitroanilines, N-phenyl-carbamates, thiolcarbamates, halocarboxylic acids, triazines, amides, ureas, diphenyl ethers, triazinones, uracils, benzo- furan derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate
S-(2,3-dichlorallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazol-1-yl-methyl)-2-chloroacetanilide 2,6-dimethyl-N-(4-methylpyrazol-1-yl-methyl)-2-chloro-acetanilide 2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide
2-(2-methyl-4-chlorophenoxy-N-methoxyacetamide
2-($\alpha$-naphthoxy)-N,N-diethylpropionamide
2,2-diphenyl-N,N-dimethylacetamide
$\alpha$-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,O$^{2,6}$,O$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-($\alpha,\alpha$-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-($\alpha,\alpha,\beta,\beta$-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine 1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-S-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4'-nitrophenyl ether (salts)
4,5-dimethoxy-2-(3-α,α,β-trifluoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]N-[4-methoxy-6-methyl-1,3,5-triazin-2-yl-aminocarbonyl]-2-chlorobenzene sulfonamide
1(3-chloro-4-ethoxyphenyl)-3,3-dimethylurea
ethyl 2-methyl-4-chlorophenoxy-thioacetate

TABLE 1

List of plant names

| Botanical name | Abbreviation in table | Common name |
| --- | --- | --- |
| Abutilon theophrasti | Abutilon theoph. | velvet leaf |
| Avena fatua | — | wild oats |
| Chenopodium album | Cheno. alb. | lambsquarters |
| Chrysanthemum spp. | Chrys. spp. | marigold spp. |
| Datura stramonium | Datura str. | jimsonweed |
| Echinochloa crus galli | Echinochl. c.g. | barnyardgrass |
| Hordeum vulgare | Hord. vulg. | barley |
| Lamium spp. | Lamium spp. | dead-nettle |
| Lolium multiflorum | Lolium mult. | annual ryegrass |
| Mercurialis annua | Mercur. annua | annual mercury |
| Poa spp. | — | bluegrass |
| Polygonium persicaria | Polyg. pers. | ladysthumb, redshank |
| Sesbania exaltata | Sesbania exalt. | hemp sesbania (coffeeweed) |
| Sinapis alba | Sinapis alb. | white mustard |
| Sorghum halepense | Sorgh. halep. | johnsongrass |
| Xanthium spp. | — | cocklebur |

We claim:
1. A compound of the formula

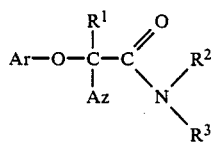
where Ar is 3,5-dichlorophenyl or 3,5-dimethylphenyl, $R^1$ is hydrogen or methyl, $R^2$ is hydrogen or $C_1$–$C_{10}$-alkyl, $R^3$ is $C_3$–$C_{10}$ alkyl and Az is triazole which is unsubstituted or substituted by halogen or methyl.
2. The compound of claim 1 which is 2-(3,5-dimethylphenoxy)-2-(1,2,4-triazol-1-yl)-acetic acid-N-tert-butylamide.
* * * * *